United States Patent [19]

Amimoto et al.

[11] Patent Number: 4,555,931
[45] Date of Patent: Dec. 3, 1985

[54] APPARATUS FOR MEASURING OR CONTROLLING THE SEPARATION RATIO OF GAS

[75] Inventors: Hiroyuki Amimoto; Hiroji Kohsaka, both of Kyoto, Japan

[73] Assignee: Horiba, Ltd., Kyoto, Japan

[21] Appl. No.: 482,313

[22] Filed: Apr. 1, 1983

[30] Foreign Application Priority Data

Apr. 21, 1982 [JP] Japan .................................. 57-66496

[51] Int. Cl.⁴ .......................................... G01N 31/00
[52] U.S. Cl. ....................................................... 73/23
[58] Field of Search ..................................... 73/23, 196

[56] References Cited

U.S. PATENT DOCUMENTS

| | | | |
|---|---|---|---|
| 2,263,335 | 11/1941 | Heinz | 73/23 |
| 2,449,067 | 9/1948 | Guillemin, Jr. | 73/23 |
| 3,300,282 | 1/1967 | Risk et al. | 73/23 X |
| 3,334,513 | 8/1967 | Thomas | 73/23 |
| 3,357,232 | 12/1967 | Lauer | 73/23 |
| 3,447,359 | 6/1969 | Kapff | 73/23 |
| 3,603,155 | 9/1971 | Morris et al. | 73/23 X |
| 3,686,930 | 8/1972 | Kniebes et al. | 73/23 X |
| 4,100,789 | 7/1978 | Joyce | 73/23 |
| 4,134,289 | 1/1979 | Bohl et al. | 73/23 |

FOREIGN PATENT DOCUMENTS

| | | | |
|---|---|---|---|
| 56-48822 | 5/1981 | Japan | 73/196 |
| 57-48634 | 3/1982 | Japan | 73/23 |
| 1444362 | 7/1976 | United Kingdom | 73/23 |

Primary Examiner—Richard L. Chiesa
Attorney, Agent, or Firm—Wenderoth, Lind & Ponack

[57] ABSTRACT

An apparatus for indirectly measuring or controlling the separation ratio of a gas to be measured or controlled when passing through a branch passage. A diluent gas with a known and adjustable flow rate is supplied to each of the branched passages through which the gas to be measured flows. The difference in the concentration of a specified gas in each of the branched passages is then measured. If the difference is equal to zero, then the separation ratio of the diluent gas is equal to the separation ratio of the gas to be measured. Alternatively, the separation ratio of the diluent gas may be set to a predetermined desired value and the flow of the gas to be measured controlled until the detected difference in concentration is equal to zero, at which point the separation ratio of the gas to be measured is equal to the separation ratio of the diluent gas.

2 Claims, 3 Drawing Figures

APPARATUS FOR MEASURING OR CONTROLLING THE SEPARATION RATIO OF GAS

BACKGROUND OF THE INVENTION

1. Field of the Invention

The present invention relates to an apparatus for measuring or controlling the separation ratio of a gas to be measured or controlled when passing through a branched passage.

2. Description of the Prior Art

The above described apparatus can be used for the measurement of the total amount of a specified gas (for example, hydrocarbon gas, $NO_x$, $SO_x$, etc.) in an exhaust gas of an engine and the like.

The total amount of the specified gas contained in an exhaust gas is determined on the basis of the flow rate of a small volume of an exhaust gas sampled from a branched passage, the measured concentration of the specified gas contained in the sampled exhaust gas and the separation ratio of the exhaust gas in the branched passage.

However, the conventional apparatus, which is provided with a capillary in each branched passage in order to measure or control the separation ratio of the gas, has a fatal defect in that a capillary is apt to be clogged in the case when the gas to be measured or controlled is a gas like an exhaust gas of an engine or a gas containing mist-like viscous substances.

SUMMARY OF THE INVENTION

It is an object of the present invention to provide a simply constructed and manufactured apparatus for measuring or controlling the separation ratio of a gas by which the separation ratio of the gas can be correctly measured or controlled regardless of the nature of the gas to be measured or controlled.

BRIEF DESCRIPTION OF THE DRAWINGS

The annexed drawings show the preferred embodiments of the present invention, in which.

DETAILED DESCRIPTION OF THE PREFERRED EMBODIMENTS

The preferred embodiments of the present invention will be described below with reference to the annexed drawings.

Figure 1:
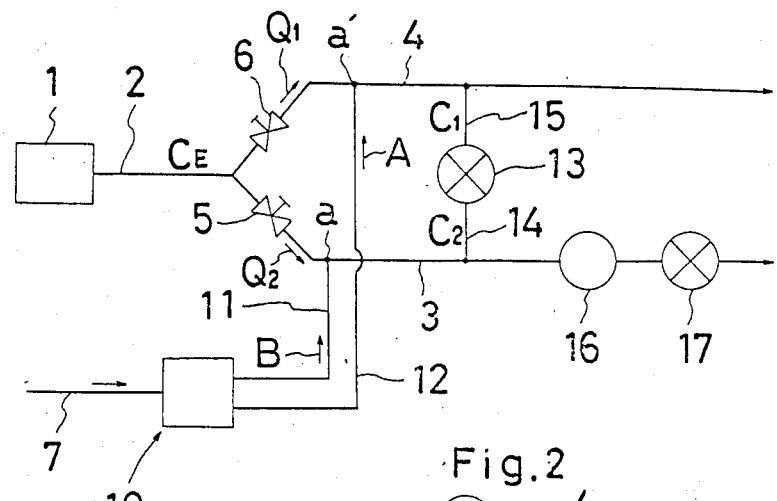
FIG. 1 is a general view showing the first preferred embodiment.

FIG. 1 shows the application of an apparatus of the present invention to a measuring instrument for measuring the total amount of a specified gas, for example, a hydrocarbon gas, contained in the exhaust gas of a car engine, wherein the exhaust gas (one example of a gas to be measured or controlled which is hereinafter referred to as the gas to be measured or controlled) is introduced into a passage 2 from an engine 1; the passage 2 is branched into a first branched passage 3 and a second branched passage 4, and the branched passages 3 and 4 are provided with throttle valves 5 and 6 therein.

On the other hand, a passage 7 for passing a diluent gas (one example of a mixture gas which is hereinafter referred to as the mixture gas) such as nitrogen gas is connected to a flow rate ratio adjusting apparatus 10 provided with a capillary for each branch (not shown) and the like; mixture gas passages 11 and 12 are respectively connected to the branched passages 3 and 4 downstream of the flow rate ratio adjusting apparatus 10; the mixture gas passage 11 is connected to the first branched passage 3 and the mixture gas passage 12 is connected to the second branched passage 4 in order to introduce the gas, which was exhausted from the flow rate ratio adjusting apparatus 10, into the gas to be measured or controlled and which is passing through the branched passages 3 and 4 downstream of the throttle valves 5 and 6.

The flow rate adjusting apparatus 10 may be merely two valves arranged in a fashion similar to valves 5 and 6 and a capillary tube for each branch or may be a more sophisticated arrangement. In any event, it is necessary for the apparatus 10 to measure and control the flow rates A and B.

Gas introducing passages 14 and 15 of a gas concentration detector 13, such as a flow modulation gas analyzer of the double-cell type disclosed in Japanese Patent Publication No. 48,822/1981, are connected to the branched passages 3 and 4 downstream of the points a and a' where the mixture gas passages 11 and 12 are connected to the branched passages 3 and 4 so that the difference in the concentration $\Delta C$ (to be described later) of the specified gas (for example, $CO_2$ gas contained in the exhaust gas of an engine) contained in a gas mixture (the gas to be measured or controlled + the mixture gas) passing through the branched passages 3 and 4 downstream of said connecting points a and a' may be measured.

Furthermore, the first branched passage 3 is provided with a flow meter 16 for measuring the amount of gas passing through the passage 3 per unit time and the passage 3 is also provided with a second concentration detector 17 for measuring the concentration of the specified gas contained in the gas to be measured or controlled.

In such a case, the following relationships are reached between the flow rate $Q_2$ of the gas to be measured or controlled and passing through the first branched passage 3 upstream of the connecting point a, the flow rate $Q_1$ of the gas to be measured or controlled and passing through the second branched passage 4 upstream of the connecting point a', the flow rate A of the mixture gas passing through the mixture gas passage 12, the flow rate B of the mixture gas passing through the mixture gas passage 11, the concentration $C_1$ of $CO_2$ (for example) contained in the gas mixture passing through the second branched passage 4 downstream of the connecting point a', the concentration $C_2$ of $CO_2$ contained in the gas mixture passing through the first branched passage 3 downstream of the connecting point a and the concentration $C_E$ of $CO_2$ contained in the gas to be measured or controlled and passing through the passage 2:

$$C_1 = \frac{Q_1 C_E}{(Q_1 + A)}$$

$$C_2 = \frac{Q_2 C_E}{(Q_2 + B)}$$

In addition, the difference in the concentration of $CO_2$ ($\Delta C$) is expressed by the following equation:

$$\Delta C = C_1 - C_2$$
$$= \frac{Q_1 C_E}{(Q_1 + A)} - \frac{Q_2 C_E}{(Q_2 + B)}$$
$$= \frac{(Q_1 B - Q_2 A) C_E}{(Q_1 + A)(Q_2 + B)}$$

This difference in the concentration of $CO_2$ ($\Delta C$) is equal to zero under the following conditions:

$Q_1 B - Q_2 A = 0$ when $Q_1$, $Q_2$ A, B are not zero, in short $Q_1/Q_2 = A/B$.

That is to say, the separation ratio of the gas to be measured or controlled is equal to the separation ratio of the mixture gas when the difference in the concentration ($\Delta C$) of $CO_2$ contained in the gas mixture measured by the concentration detector 13 is equal to zero.

Accordingly, the separation ratio $Q_1/Q_2$ of the gas to be measured or controlled can be measured on the basis of the separation ratio of the mixture gas by adjusting the separation ratio A/B of said mixture gas by means of the flow rate ratio adjusting apparatus 10 so that a difference in the concentration ($\Delta C$) of $CO_2$ which is equal to zero may be detected by the concentration detector 13. Then, the total amount of hydrocarbon gas contained in the exhaust gas of car engine can be determined on the basis of this separation ratio $Q_1/Q_2$, the flow rate of the gas mixture measured by the flow meter 16, the concentration of hydrocarbon gas measured by the concentration detector 17, the flow ratio of the mixture gas and the separation ratio of the mixture gas.

The case in which the separation ratio $Q_1/Q_2$ of the gas to be measured or controlled is measured was described in the above described preferred embodiment. Described below with reference to FIG. 1 is the case in which the separation ratio $Q_1/Q_2$ of the gas to be measured or controlled is controlled.

The separation ratio $Q_1/Q_2$ ($=K$) of the gas to be measured or controlled can be controlled to a desired value by setting the separation ratio ($A/B=K$) of the mixture gas to the desired value by means of the flow rate ratio adjusting apparatus 10 and simultaneously manually or automatically adjusting the opening of the throttle valves 5 and 6 so that a difference in the concentration ($\Delta C$) of $CO_2$ which is equal to zero may be detected by means of the concentration detector 13.

Furthermore, the specified gas component contained in the gas to be measured or controlled and the mixture gas are not limited to $CO_2$ gas and the diluent gas, such as $N_2$ gas, used in the above described preferred embodiment. For example, a gas which is not contained in gas to be measured or controlled but contained only in the mixture gas may be measured, or a gas which is contained in both the gas to be measured or controlled and the mixture gas may be used as the specified gas component.

Figure 2:
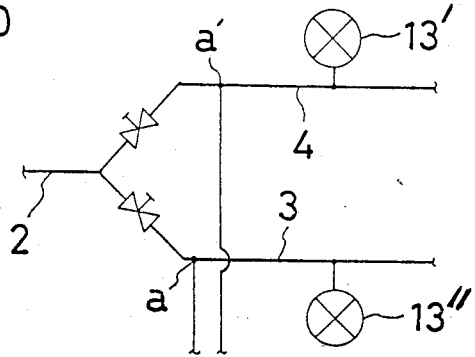
FIG. 2 is a diagram showing the important parts of another preferred embodiment.

FIG. 2 shows another preferred embodiment of the present invention, in which the difference in the concentration ($\Delta C$) of the specified gas component contained in the mixture gas is detected by two concentration detectors 13' and 13" installed in the branched passages 3 and 4 and arranged downstream of the connecting points a, a' as shown in FIG. 1.

Figure 3:
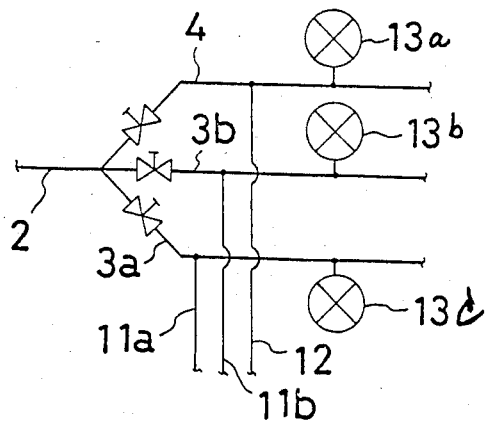
FIG. 3 is also a diagram showing the important parts of still another preferred embodiment.

FIG. 3 shows still another preferred embodiment of the present invention, in which a passage 2 for passing the gas to be measured or controlled therethrough is branched into three branched passages 3a, 3b, and 4; the branched passage 3a is connected to a mixture gas passage 11a; the branched passage 3b is connected to a mixture gas passage 11b; the branched passage 4 is connected to a mixture gas passage 12; concentration detectors 13a, 13b, and 13c for detecting the concentration of the specified gas component contained in a gas mixture are respectively installed to detect the difference in the concentration of the specified gas component in the branched passages 3a, 3b and 4; the separation ratio of the gas to be measured or controlled can be thereby measured or controlled as in the case shown in FIG. 1.

As described above, the present invention can provide an apparatus for measuring or controlling the separation ratio of a gas, wherein each branched passage is connected to each mixture gas passage and a concentration detector for detecting the difference in the concentration of the specified gas component contained in the gas mixture passing through the branched passages is installed downstream of the point where the mixture gas passage is connected with the branched passage. Thus, as described in the above described preferred embodiment, the separation ratio of the mixture gas is equal to that of the gas to be measured or controlled under the condition that the difference in the concentration of the specified gas component is equal to zero and, as a result thereof, the separation ratio of the gas to be measured or controlled can be determined on the basis of the separation ratio of the mixture gas. In addition, the separation ratio of the gas to be measured or controlled can be controlled to the desired value by setting the separation ratio of the mixture gas to the desired ratio and adjusting the separation ratio of the gas to be measured or controlled so that the difference in the concentration is equal to zero.

That is to say, according to the present invention, the separation ratio of gas to be measured or controlled is indirectly measured or controlled on the basis of the separation ratio of the mixture gas. Thus, unlike the case of conventional apparatus, it is not necessary for a capillary to be installed in a passage of the gas to be measured or controlled. Accordingly, stained gas, such as an exhaust gas of an engine, can be selected as the object of measurement or control. In short, according to the present invention, the separation ratio of the gas to be measured or controlled can be correctly measured or controlled regardless of the nature of the gas to be measured or to be controlled. Furthermore, the present invention has such an advantage that the separation ratio can be simply and correctly measured or controlled even though the flow rate of the gas to be measured or controlled is unstable.

We claim:

1. An apparatus for indirectly measuring the separation ratio of a first gas containing a specified gas whose path is branched into at least two branches, said separation ratio being defined as the ratio of the gas flow rate in one of said at least two branches divided by the gas flow rate in another of said at least two branches, and said apparatus comprising:

a mixture gas supply means for respectively supplying a mixture gas with a known and adjustable flow rate and separation ratio to each of said at least two branches, said separation ratio being defined as the ratio of the gas flow rate in one of said at least two branches divided by the gas flow rate in another of said two branches, and;

a gas concentration detector means operatively connected to said at least two branches downstream of said mixture gas supply means for measuring the difference in concentration of said specified gas in said at least two branches;

wherein, when said mixture supply means is adjusted so that said detector means measures a zero difference in concentration in said at least two branches, then said separation ratio of said first gas corresponds to said separation ratio of said mixture gas from said mixture gas supply means.

2. An apparatus for controlling the separation ratio of a first gas containing a specified gas whose path is branched into at least two branches, said separation ratio being defined as the ratio of the gas flow rate in one of said at least two branches divided by the gas flow rate in another of said at least two branches, and said apparatus comprising:

a mixture gas supply means for respectively supplying a mixture gas with a known and adjustable flow rate and separation ratio to each of said at least two branches, and separation ratio being defined as the ratio of the gas flow rate in one of said at least two branches divided by the gas flow rate in another of said at least two branches, and;

a gas concentration detector means operatively connected to said at least two branches downstream of said mixture gas supply means for measuring the difference in concentration of said specified gas in said at least two branches;

a means for controlling the flow rate of each of said at least two branches, said means arranged upstream of said mixture gas supply means;

wherein, when said flow rates of said mixture supply means are adjusted so that the separation ratio of said mixture gas supply means corresponds to a desired separation ratio of said first gas and said means for controlling the flow rate of each of said at least two branches are controlled so that said detector means measures a zero difference in concentration in said at least two branches, then said separation ratio of said first gas corresponds to said separation ratio of said mixture gas from said mixture gas supply means.

* * * * *